(12) United States Patent
East et al.

(10) Patent No.: US 6,245,077 B1
(45) Date of Patent: Jun. 12, 2001

(54) UNIVERSAL MYRINGOTOMY TUBE/AURAL GROMMET INSERTER AND METHODS

(75) Inventors: Matthew Scott East, Taunton; Edward Pennington-Ridge, Watchet, both of (GB)

(73) Assignee: Exmoor Plastics Ltd., Taunton (GB)

( * ) Notice: Subject to any disclaimer, the term of this patent is extended or adjusted under 35 U.S.C. 154(b) by 0 days.

(21) Appl. No.: 09/489,126

(22) Filed: Jan. 21, 2000

(51) Int. Cl.[7] ............................................. A61F 11/00
(52) U.S. Cl. ...................................................... 606/109
(58) Field of Search ....................... 606/108, 109, 606/207, 205, 210; 81/345, 355, 424.5

(56) References Cited

U.S. PATENT DOCUMENTS

| | | | |
|---|---|---|---|
| 2,243,305 | * | 5/1941 | Adler . |
| 4,268,955 | * | 5/1981 | Daniels . |
| 5,383,886 | * | 1/1995 | Kensey et al. ................. 606/185 |
| 5,437,682 | * | 8/1995 | Grice et al. .................... 606/148 |

FOREIGN PATENT DOCUMENTS

| | | | |
|---|---|---|---|
| 99281 | * | 9/1898 | (DE) ............................. 606/205 |
| 3007994 | * | 9/1980 | (DE) ............................. 606/108 |
| 3812165 | * | 10/1989 | (DE) ............................. 606/205 |

* cited by examiner

Primary Examiner—Jeffrey A. Smith

(57) ABSTRACT

An instrument for grasping securely an aural ventilation tube whilst simultaneously presenting the device at the correct angle for the insertion of an aural ventilation tube. The instrument prevents a rotation of the aural ventilation tube during the insertion procedure.

The instrument is able to be passed from one medical practitioner to another during the procedure.

9 Claims, 4 Drawing Sheets

US 6,245,077 B1

UNIVERSAL MYRINGOTOMY TUBE/AURAL GROMMET INSERTER AND METHODS

The Universal Aural Grommet Inserter is utilised to insert transtympanic aural grommets in an ear to ventilate the middle ear and relieve pain and infection.

There are a multitude of varying designs of aural ventilation tube and this new Universal Aural Grommet Inserter is designed to enable a competent medical practitioner to insert most types of aural ventilation tube within an ear.

The device is similar in appearance to a commonly utilised instrument with which all Ear, Nose and Throat Surgeons are familiar, namely a suction tube hand-piece. The device is intended to be single use and is operated by a slide control on the hand-piece of the Universal Aural Grommet Inserter. The slide control is intended to advance and retract a 0.5 mm curved stainless steel wire to grasp and release the aural grommets. The use of this device will obviate the need for conventional forceps and ensure optimum grasping angle for presentation of the aural grommet to the ear drum.

BACKGROUND TO THE INVENTION

An aural ventilation tube can take many forms but it is intended to be inserted into the human ear drum for the purpose of ventilating the middle ear cleft. In short, it maintains an airway between the middle ear and the external ear canal. It may be called a 'drain', which is a misnomer; a 'vent tube'; a 'p.e. (pressure equalization) tube' or a 'grommet'.

Aural ventilation tubes/grommets are normally inserted with surgical alligator forceps (see FIG. 1). Especially designed inserters have been used, which transport the ventilation tube/grommet by means of a metal pin (see FIG. 2), having an interference fit with the lumen or bore, i.e. the internal diameter of the tube. Once in situ, the pin is withdrawn from the lumen into a tube, the distal end of which, pressing against the outer flange of the grommet, thereby prevents its dislodgement from the incision in the ear drum, so leaving the ventilation tube/grommet in situ.

The ear drum closes the external ear canal, forming a beveled end to the canal. Existing inserters, which fit the internal diameter of the vent tube, are rarely used because they present the leading or inner flange of the ventilation tube/grommet to the ear drum at the wrong angle, which means that it is difficult or, for some clinicians, impossible to locate the device across the ear drum, owing to the length of the narrow, external ear canal, which severely limits the surgeon's ability to manipulate the grommet into the incision in the ear drum.

BRIEF SUMMARY OF THE INVENTION

The object of the invention is to provide a convenient and economic method by which to insert an aural ventilation tube/grommet. The invention constitutes a more secure, stable and hygienic means of transporting and inserting an aural grommet, whilst improving the ergonomics of the procedure.

DETAILED DESCRIPTION OF THE INVENTION

Figure 1:
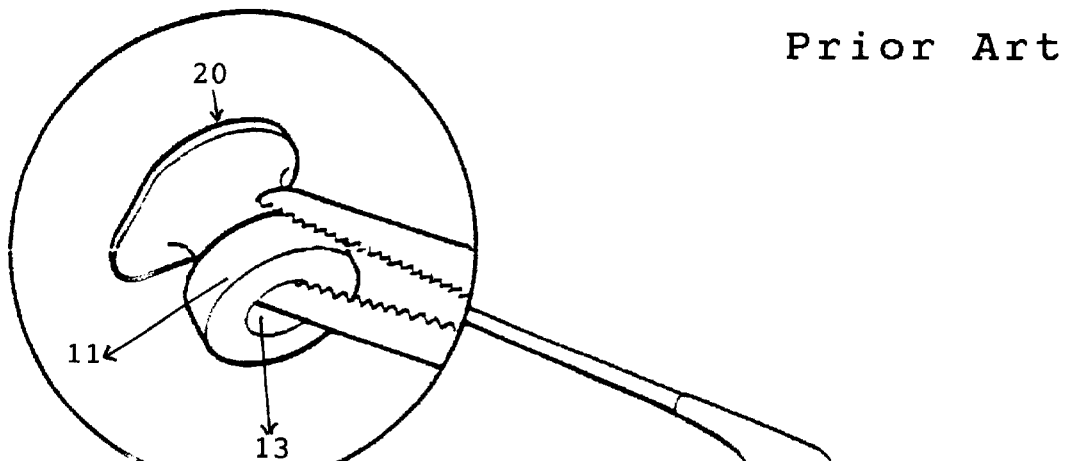
FIG. 1 Micro Alligator Forceps holding Shah type aural ventilation tube. (Prior Art)
Figure 2:
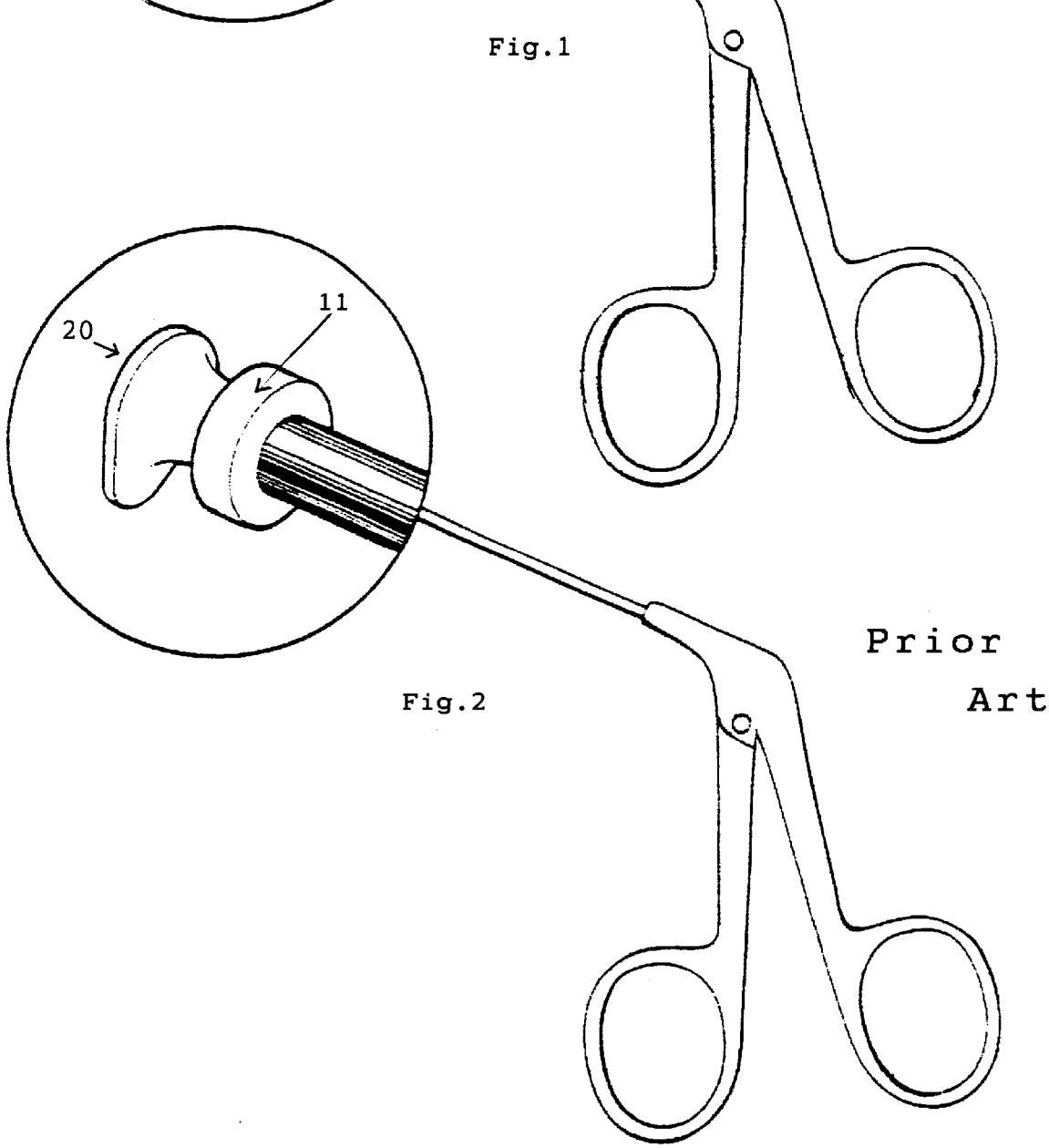
FIG. 2 Scissor action piston type aural ventilation tube inserter holding a Shah type aural ventilation tube. (Prior Art)

The invention comprises a universal ventilation tube/aural grommet insertion instrument (FIG. 5) used for the placement of a ventilation tube/aural grommet 11 across the tympanic membrane transtympanic placement.

The invention takes the form of a micro-bore tube 1 for which a weld-free, stainless steel tube 1 of 18 s.w.g. (1.24 mm outside diameter) is preferred, although other validated, rigid materials and similar dimensions would be suitable. A handle 2 is moulded to the tube 1 manufactured from blue, high density polyethylene, which facilitates the surgeon's firm grip on the instrument (FIG. 4), but the colour, shape, size and material content of the handle 2 may be changed without affecting the instrument's (FIG. 4) characteristics significantly, providing that they afford a firm grasp for the surge on and prevent the tube 1 from rotating within the handle 2.

The tube 1 is bent or curved 3 at a preferred distance of approximately 60 mm from its distal end 4 sufficient to allow a clear line of sight along the tube 1 at its distal end 4 without obstruction to that view from the hand of the us er.

Figure 3:
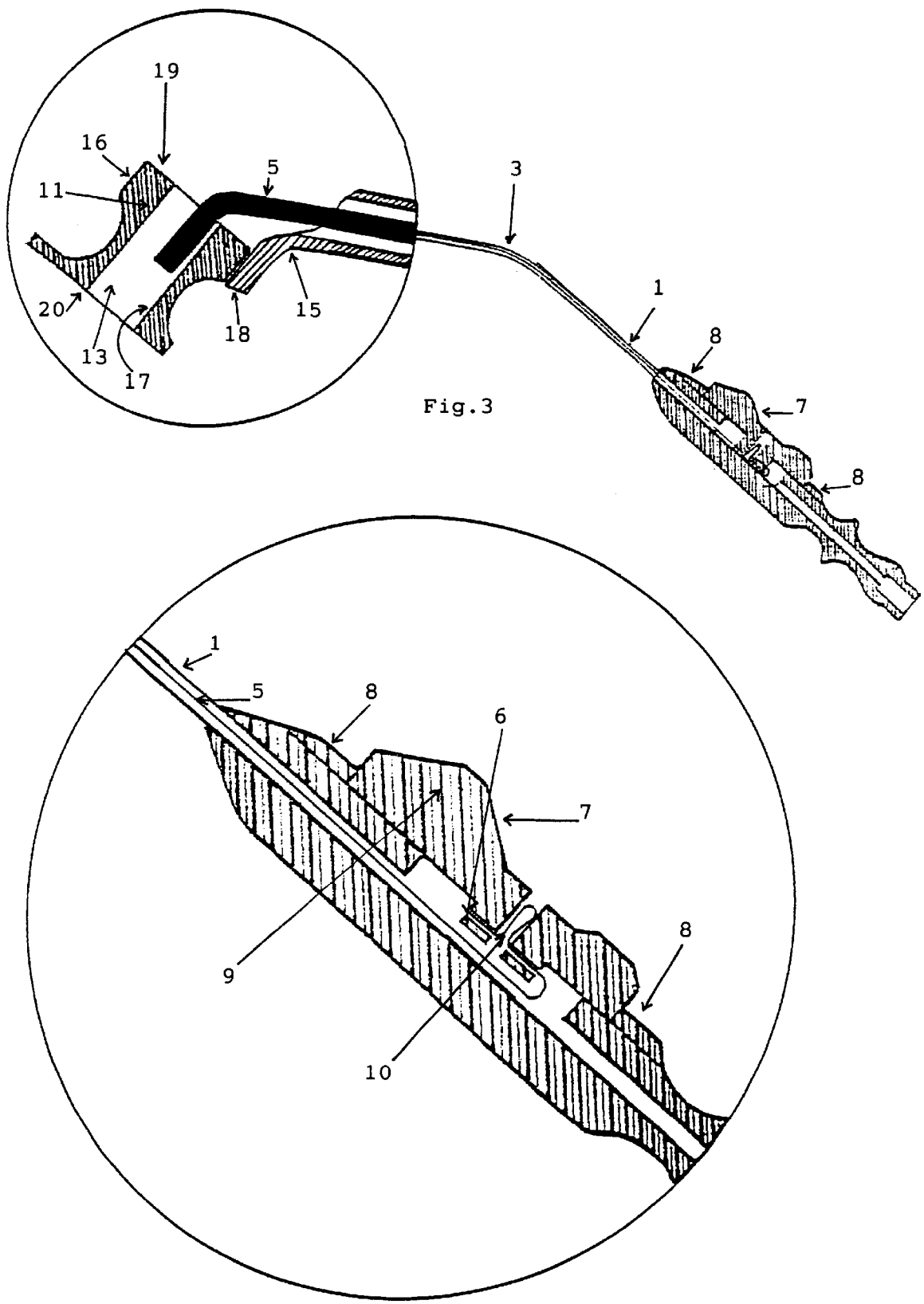
FIG. 3 Cross section of Universal Aural Ventilation Tube/Grommet Inserter with enlarged detail.

A piston 5 is located within the tube, which projects from the distal end 4. This piston 5 may be made of any rigid validated material and may be solid or hollow. For this purpose, however, stainless steel wire 5 of 0.5 mm diameter has been preferred. At its proximal end 6, which is within the handle, this wire piston 5 is connected to a finger-operated slide 7. The slide 7 moves forwards and backwards within a supporting recess 8 in the plastic handle 2 of the instrument, which breaches the stainless steel tube 1 within it, forming a slot in that tube 1. This allows the slide 7 and wire 5 which comprise the piston assembly 9, which includes 5, 6, 7 and 10, to move backwards and forwards. The slide component 7 is made of blue, high density polyethylene but could be made of any other validated rigid material. A hole 10 through that slide component 7, perpendicular to the axis of the tube 1, accepts and traps the wire piston 5, which is bent and folded on itself but which, springing apart, within the hole 10 through the slide component 7, makes a positive connection between the slide 7 and the piston 5 (see FIG. 3).

Figures 4, 5:
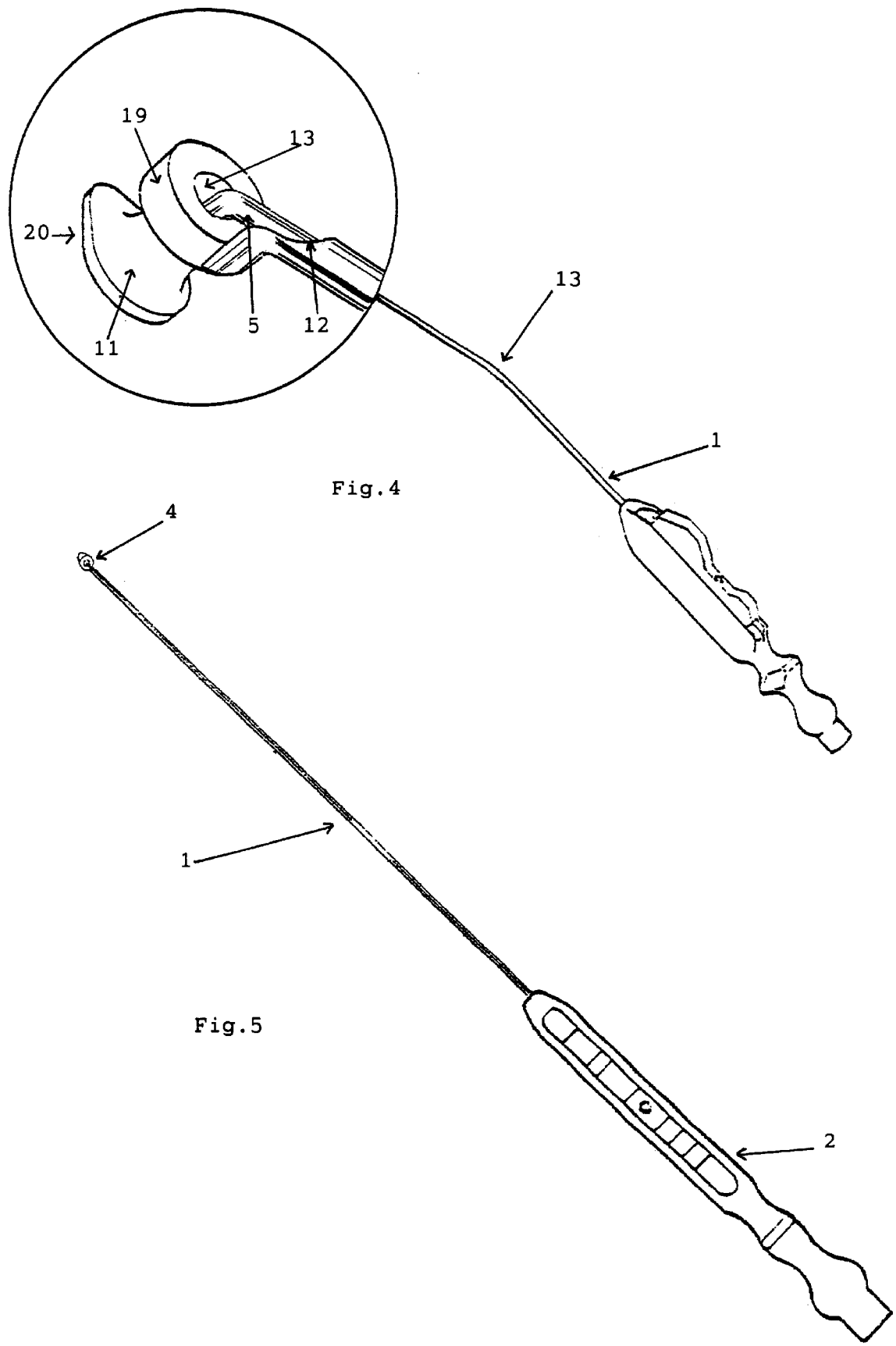
FIG. 4 Perspective view of Universal Aural Ventilation Tube/Grommet Insertion Instrument with enlarged detail of jaws and Shah type ventilation tube/grommet.
FIG. 5 Plan view of Universal Aural Ventilation Tube Insertion Device.
Figures 6, 7:
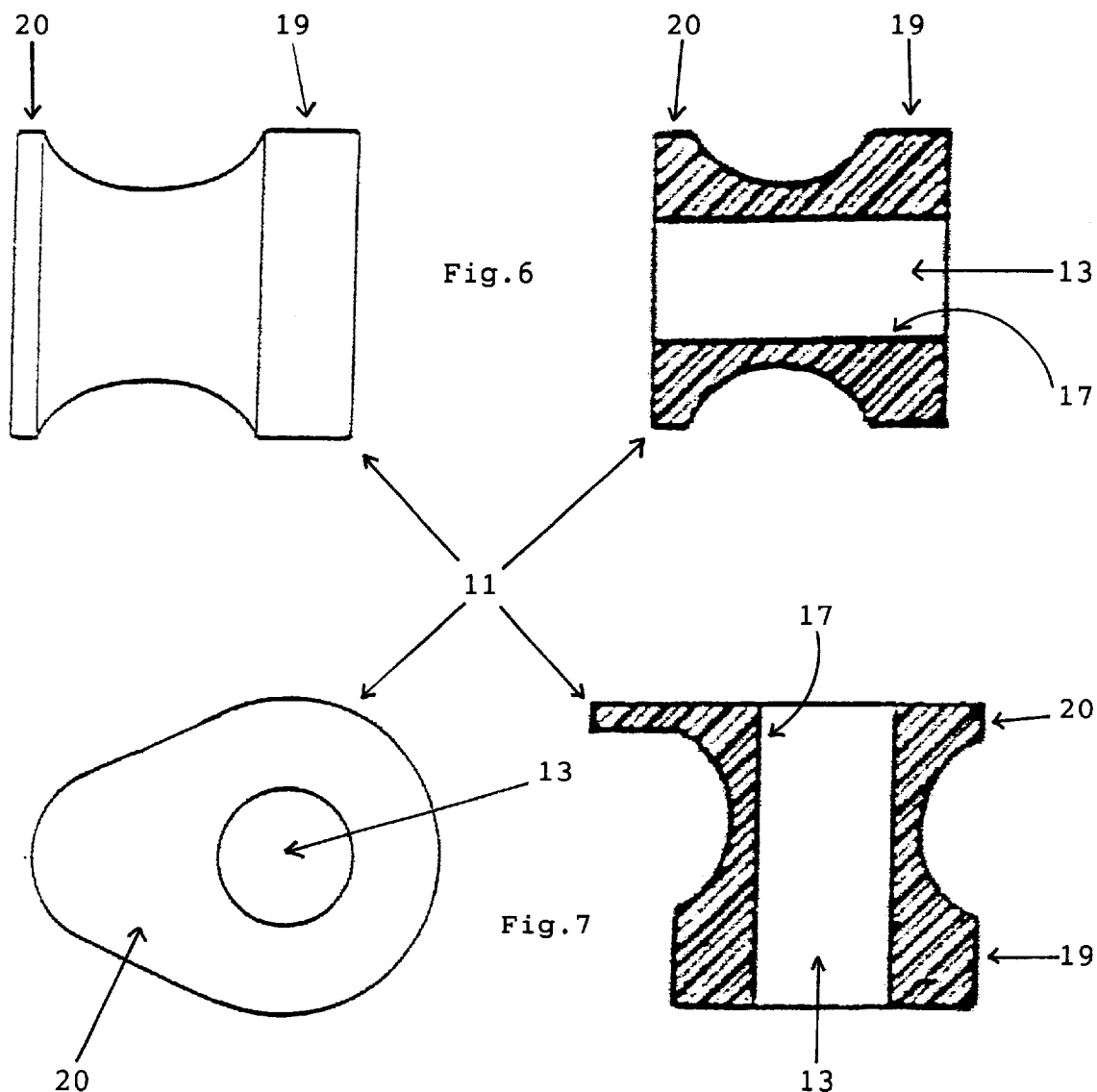
FIG. 6 Side elevation and cross section of a typical aural ventilation tube/grommet (Shepards Drain).
FIG. 7 Plan view of inner flange of aural ventilation tube (Shah) and cross section of aural ventilation tube (Shah).

With the slide 7 pushed forward, the wire piston 5 protruding from the distal end 4 is cut to length, according to the dimensions of the ventilation tube/grommet to be inserted by the instrument (FIG. 4). In the case of this instrument (FIG. 4), that projection is between 1.7 mm and 1.8 mm from the distal end 4 of the tube 1, when fully advanced. These dimensions may vary according to the pattern of aural ventilation tube/grommet 11 to be inserted.

Any other mechanical design for advancing and withdrawing the piston by single-handed movement would be equally satisfactory.

The distal end 4 of the instrument (FIG. 4) is ground away 12 to enable it to be angled to a preferred 45° or similar angle. The shape of this angled protrusion 15 will have a radius 18 to accommodate the outer flange 19 of any aural ventilation tube/grommet 11.

The method for inserting the ventilation tube/grommet 11 is as follows. The surgeon or clinical assistant holds the inserter (FIG. 4) in one hand and manually advances the piston assembly 9 by using a forefinger to press the slide component 7 forward towards the distal end 4 of the instrument. The projecting piston 5 is then fully introduced into the lumen 13 of the ventilation tube/grommet 11. With the piston assembly 9 free to move, the ventilation tube/grommet 11 is grasped between the angled distal end of the tube 18 and the angled distal end of the piston wire 5, when it is retracted so that the immobile jaw 18 of the grasping mechanism (FIG. 3) comes to rest against the annulus 16 of the external flange 19 of the ventilation tube/grommet 11 and the other mobile jaw 5 comes to rest against the internal surface 17 of the external flange 19 of the ventilation tube/grommet 11 (see FIG. 3).

The piston 5 of the instrument (FIG. 4) makes a secure fit within the external flange 19 of the ventilation tube/grommet 11. The registration of the external flange 19 of the ventilation tube/grommet 11 against the immobile jaw 18 of the instrument (FIG. 4) assures that the ventilation tube/grommet 11 cannot rotate during its introduction into the incision in the ear drum.

When the inner flange 20 of the ventilation tube/grommet 11 has been introduced into the incision, the surgeon holds the instrument (FIG. 4) still while manually advancing the piston assembly 9 and, by that means, the piston 5 from the lumen 13 of the ventilation tube/grommet 11. This releases the grip of the ventilation tube/grommet 11, leaving it lying partially within the incision in the ear drum. Gentle pressure on the visible part of the inner flange 20 forces the ventilation tube/grommet 11 into position across the ear drum, thereby completing the insertion procedure.

We claim:

1. An insertion instrument for the placement of an aural ventilation tube or grommet across the tympanic membrane of a patient by a practitioner, said instrument comprising:

a tube having a longitudinal axis, a proximal end, and a distal end;

a handle attached to said proximal end of said tube;

a finger-operated slide located adjacent said handle; and a piston located within said tube and having a proximal end attached to said finger-operated slide, and a distal end for projecting from said distal end of said tube; and wherein said distal end of said tube and said distal end of said piston comprise means for grasping said aural ventilation tube or grommet for insertion across the tympanic membrane of said patient.

2. The insertion instrument according to claim 1, wherein said grasping means comprises jaws, one of said jaws capable of being advanced and retracted relative to another of said jaws.

3. The insertion instrument according to claim 1, wherein said grasping means comprises an upper jaw associated with said distal end of said piston and a lower jaw associated with said distal end of said tube, wherein said lower jaw is immobile relative to said tube and has a profile such that unwanted rotation of said aural ventilation tube or grommet upon insertion into the tympanic membrane of said patient is prevented.

4. The insertion instrument according to claim 1, wherein said grasping means is independent of the profile of said aural ventilation tube or grommet making it capable of grasping different patterns of aural ventilation tubes or grommets.

5. The insertion instrument according to claim 1, wherein said instrument is disposable.

6. The insertion instrument according to claim 1, wherein said instrument further comprises means for grasping said aural ventilation tube or grommet at a correct angle for insertion until such time as said practitioner releases said aural ventilation tube or grommet within an incision in the tympanic membrane of said patient.

7. A method of grasping an aural ventilation tube or grommet, comprising the steps of:

providing the insertion instrument according to claim 6;

pre-loading said insertion instrument with an aural ventilation tube or grommet for insertion across the tympanic membrane of said patient by said practitioner.

8. A method of grasping an aural ventilation tube or grommet according to claim 7, further comprising the step of pre-loading said insertion instrument with said aural ventilation tube or grommet at a correct angle with respect to said longitudinal axis such that said aural ventilation tube or grommet is held at said correct angle until such time as said practitioner releases said aural ventilation tube or grommet within an incision in the tympanic membrane of said patient.

9. A method of inserting an aural ventilation tube or grommet across the tympanic membrane of a patient by a practitioner, comprising the steps of:

providing the insertion instrument according to claim 6;

pre-loading said insertion instrument with an aural ventilation tube or grommet for insertion across the tympanic membrane of said patient by grasping said aural ventilation tube or grommet such that said aural ventilation tube or grommet remains held at a correct angle for insertion; and inserting said aural ventilation tube or grommet within an incision in the tympanic membrane of said patient.

* * * * *